United States Patent [19]
White

[11] Patent Number: 5,727,944
[45] Date of Patent: Mar. 17, 1998

[54] DENTAL IMPRESSION SHROUD

[76] Inventor: Dennis J. White, 51 Nostrano Rd., Cranbury, N.J. 08512

[21] Appl. No.: 722,854

[22] Filed: Sep. 26, 1996

[51] Int. Cl.⁶ .................................................... A61C 9/00
[52] U.S. Cl. ............................ 433/214; 433/37; 433/136
[58] Field of Search ............................ 433/7, 37, 41, 433/136, 138, 139, 214

[56] References Cited

U.S. PATENT DOCUMENTS

| | | | |
|---|---|---|---|
| 2,092,549 | 9/1937 | Craigo | 433/136 |
| 2,423,005 | 6/1947 | Chaiken | 433/41 |
| 3,056,205 | 10/1962 | Ennor | 433/37 |
| 3,772,790 | 11/1973 | Swan-Gett et al. | 433/136 |
| 4,600,387 | 7/1986 | Ross | 433/136 |
| 5,580,243 | 12/1996 | Bloore | 433/7 |

*Primary Examiner*—John J. Wilson

[57] ABSTRACT

A new type of dental impression device is disclosed, which aides in producing more accurate impressions. The device is a spring loaded device which holds a panel flat against the teeth. This panel is custom fabricated to fit against the teeth just below the height of contour. It temporarily yields a flattened surface, masking all of the irregular surfaces beneath it. The dental impression material may then be removed without the distortion caused by the associated stretching over the curves of the teeth.

10 Claims, 3 Drawing Sheets

DENTAL IMPRESSION SHROUD

FIELD OF INVENTION

This invention relates to taking accurate dental impressions, from which indirect dental prosthesis are fabricated.

DESCRIPTION OF PRIOR ART

Heretofore, dental impressions are taken with various forms of dental trays filled with moldable material. The trays used are either pre-made stock trays or custom trays, individually made from a study model.

These impression techniques yield castings or restorations that usually require adjustments, done by the dentist, at time of cementation. This is due to the inherent distortion of the impression technique.

Distortion of dental impressions are caused by forces exerted on the impression material at the time it is lifted from the teeth. Forces are created due to vacuum formed over teeth upon tray removal. Further deformation also occurs as impression material stretches to accommodate undercuts of teeth.

In the recent disclosure by White, application Ser. No. 08/396,478, now U.S. Pat. No. 5,580,244, more accurate castings are now possible with use of a vented tray. This method and apparatus eliminates vacuum over teeth upon tray removal. Although restorations need less adjustment, and the process is more tolerable, further refinement is needed.

Present day techniques do not address the matter of undercuts of the adjacent teeth and oral structures. Impression materials are not resilient enough to compensate for the irregular patterns of the mouth.

In U.S. Pat. No. 3,772,790 Swan-Gett, et al., disclose a tooth isolating shield. This disclosure reveals an isolation device to be used during operative dentistry, covering all of the uninvolved teeth. It covers total areas of teeth and can not be used to mask dental undercuts. It would not be an aid in taking dental impressions.

In U.S. Pat. No. 2,092,549, Craigo discloses a form of dental dam, which isolates several teeth. The invention covers the immediate oral structures, but does not mask the undercuts of adjacent teeth.

In U.S. Pat. No. 4,600,387, Ross shows a form of rubber dam that would also isolate teeth and cover the surrounding oral structures. However, this invention does not cover the lower portions of teeth and thus would not mask undercuts.

OBJECTS AND ADVANTAGES

"One of the most frustrating aspects of dentistry is the restoration that does not fit its preparation. The problem remains despite the introduction of impression materials, such as the polyvinylsiloxane, with low polymerization contraction and excellent stability." R. W. Wassel, et al., J Prosthetic Dent 1991;65:748–757.

Currently used impression trays inflict trauma to impression material during removal from the mouth. This trauma stresses and distorts impression materials beyond its elastic memory limits, eventually engendering a casting which is inaccurate.

Diagnosis of origin of inaccuracy of castings is difficult due to the complex series of steps involved. Distortion can occur in many areas of the fabrication process. "Making a casting involves a series of controlled compensations for the dimensional changes occurring throughout the process. Because there is always a discrepancy between the tooth and the cast restoration its fit . . . has become an intense preoccupation." Hunter, et. al. J Prosthet Dent 1990;64:636–641.

Diagnosis is further limited because of randomness of final fit. Many restorations do fit well and is supportive of present day techniques. Yet, many have an unexplainable poor fit. Dentists and manufacturers have not isolated the damaging effect of impression tray removal.

The dental impression shroud of present invention will mask undercuts. By eliminating appropriate undercuts and by using a vented impression tray, accurate restorations are possible. The disclosure herein shows a spring activated appliance that is readily fitted in place in the oral cavity and is readily removed.

The reader will see that the use of present invention will aid dentists and laboratory technicians in the process of fabricating restorations. Fit is predictable, leaving dentist with a more controllable means to fabricate a quality casting.

The object of this invention is to produce a clinically acceptable restoration from the laboratory with a minimum to no adjustment.

DETAILED DESCRIPTION OF THE PREFERRED EMBODIMENT

Figure 1:
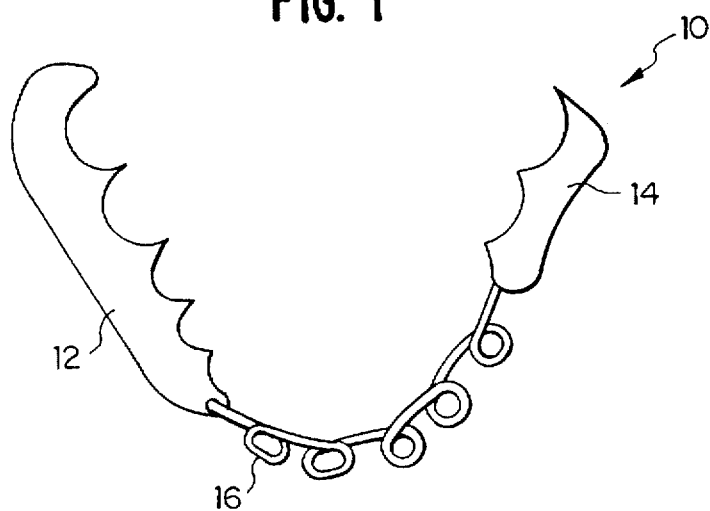
FIG. 1 is a top view of present invention.

Referring to the drawings in general and to FIGS. 1 to 6 in particular, is a dental impression shroud of the present invention.

FIG. 1 shows a dental shroud, 10 to be used to block undercuts on the buccal aspects of the lower right quadrant.

Figure 2:
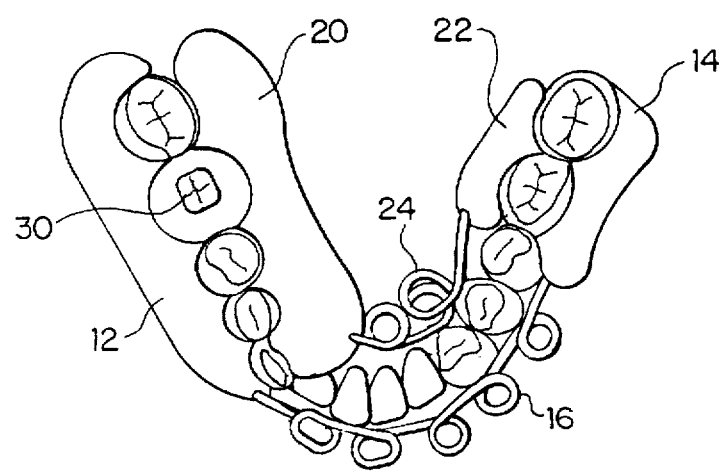
FIG. 2 is a top view of present disclosure, in place over teeth.

From an accurate study model, the tooth to be restored is identified, in FIG. 2 this is the lower right first molar, 30. Methylmethacrylate, 12, is added on the buccal aspect to this area of the model. It is positioned to mask undercuts of both the adjacent teeth and nearby soft tissue. It is trimmed and shaped to the borders of the mucosa not to go over the height of contour of the teeth. It is also trimmed a few millimeters apical of the free gingival crest of the tooth or teeth to receive impressions.

A smaller reciprocal pad is fabricated on the opposite side of the arch, 14. This methylmethacrylate pad is designed to cover a few teeth and to engage interproximal curves to aid stability.

A spring, 16, is stretched slightly open to meet buccal shroud plate, 12, and reciprocal pad, 14. The ends of the spring are attached to the pieces by use of methylmethacrylate. Ends of the spring are kept toward the anterior as to not interfere with the smooth surface of shroud in area of prepared tooth to be impressed.

If the anatomy of the arch dictates, another shroud may be fabricated and applied to the lingual surface of the teeth. The fabrication process is the same for a lingual shroud. The lingual shroud spring, 24, must be more flexible since the anterior ends of right and left inner shroud and reciprocal pad are closer together.

Once the methylmethacrylate has set, the appliances are removed and polished. At the time of the impression for the patient, the shrouds are placed into the mouth. Any undercuts interproximal of the adjacent teeth to the prepared tooth may be filled with direct deposition of composite or luting cement. These areas may not be adequately covered by the dental shrouds.

The fit of the dental impression tray is now verified.

Figure 3:
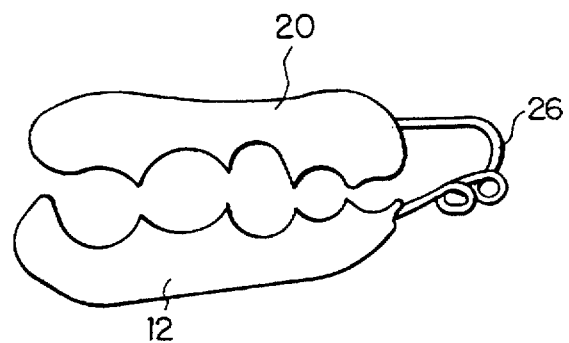
FIG. 3 is a top view of dental shroud, designed for an anterior application.

After the impression is taken, the individual impression shrouds are removed. Special attention is given to be sure any added luting cement is removed from teeth. FIG. 3 illustrates a single dental shroud with one spring, 26. This design may be more applicable in anterior regions of the mouth, where it may be more difficult to locate an opposing arch to receive the reciprocating pad.

Figure 4:
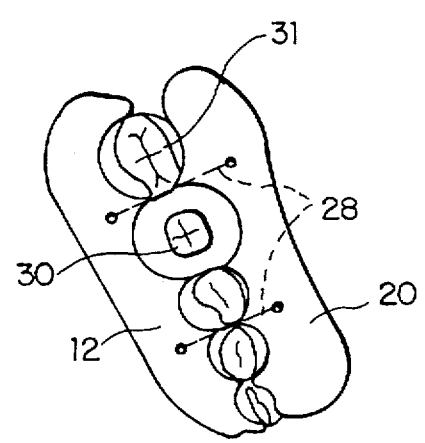
FIG. 4 is a top view of dental shroud held buccally and lingually with elastic.

FIG. 4 shows a design of the present invention, which does not utilize external springs. The shroud may be fastened by an elastic, 28, or ligature which attaches to both buccal, 12, and lingual, 20, halves and passes through a dental embrasure.

Similarly both halves may also be stabilized with a temporary luting or bonding agent. Although not illustrated, this would allow a direct placement of the shroud without fixing with a ligature. The temporary luting agent would allow a snap release after impression is taken.

Figure 5:
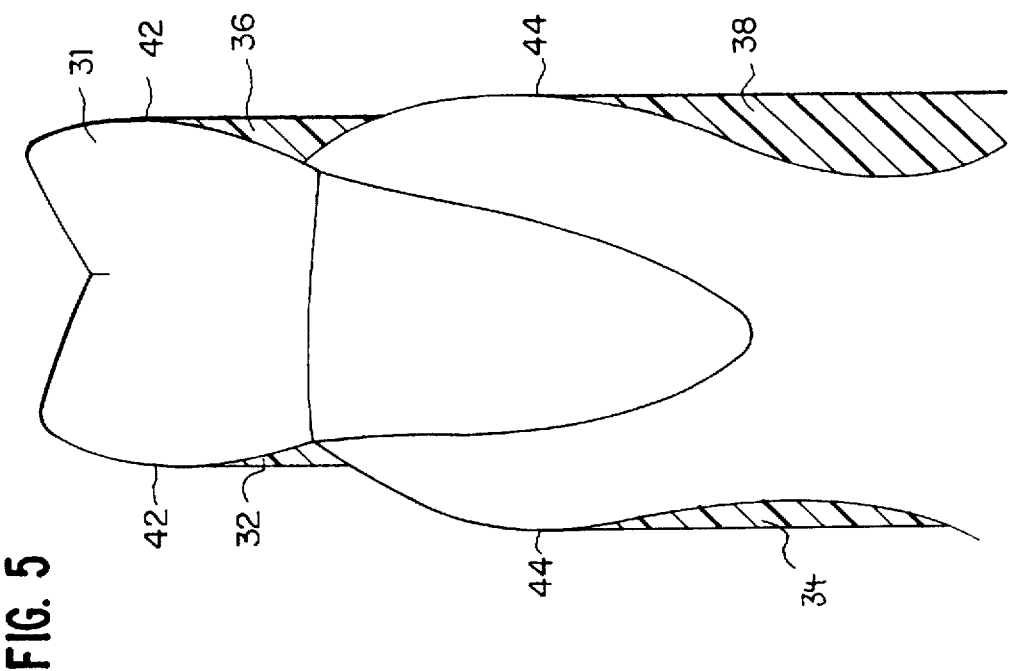
FIG. 5 is an anterior cross section view of tooth and gingiva.

FIG. 5 illustrates the areas of undercuts around the coronal aspect of tooth, 31. The undercuts, 32 on the buccal aspect of tooth 31, and, 36 on the lingual aspects of tooth 31, fall below the height of contour, 42. The buccal undercut of the soft tissue, 34, and the lingual undercut of soft tissue, 38, fall below the tissue height of contour, 44.

Figure 6:
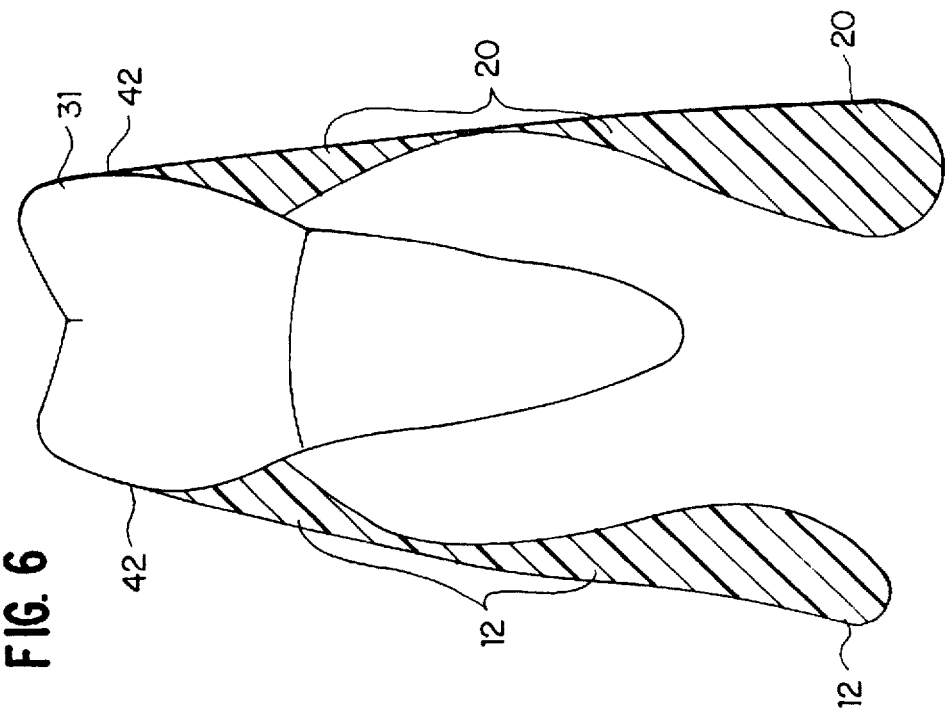
FIG. 6 is an anterior cross section view of tooth and gingiva with impression shroud in place, buccally and lingually.

FIG. 6 illustrates how all undercuts are eliminated with the application of the dental impression shroud. The buccal shroud, 12 and the lingual shroud, 20 eliminate all undercuts under the height of contour, 42.

The shroud design may be modified to mask only coronal undercuts if no tissue undercuts are present.

CONCLUSIONS, RAMIFICATION AND SCOPE OF INVENTION

Thus the reader can see that the dental impression shroud disclosed herein is versatile and can be used for onlays, crowns, and bridges. It can be used in any area of the mouth. Due to superior fit of final restorations, this impression shroud has the added benefits in that:

castings have a more predictable fit dentists take less time to seat restoration teeth will have less post-operative sensitivity because of even fitting of crown.

there is greater longevity of the restoration.

Although the description above contains many specifications, these should not be construed as limiting the scope of the invention but as merely providing illustrations of the preferred embodiments of the invention. For example, the dental shroud may be temporarily bonded in place to the teeth, eliminating the springs. The dental shroud could also be held with a ligature.

Thus the scope of the invention should be determined by the appended claims and their legal equivalents, rather than by the examples given.

I claim:

1. A dental impression shroud for masking the undercut areas of oral structures while an impression is being taken with a dental impression tray, said shroud is made of a rigid material and comprises an interior surface that is shaped to fit selected areas of oral structures and an opposite external surface which is substantially flat, wherein during use, when the interior surface is placed against the oral structures, said flat external surface forms an angle with respect to said impression tray that is slightly less than perpendicular, whereby said shroud masks the undercut surfaces and provides a flat external surface at an angle that allows the impression material within said dental impression tray to be removed without distorting to thereby provide a more accurate impression of the unmasked oral structures.

2. A dental impression shroud as claimed in claim 1 whereby said oral structures comprise the teeth and soft tissue and said shroud has a top edge and said flat surface tilts toward the teeth with said top edge of said shroud in use is positioned at the height of contour of said teeth.

3. A dental impression shroud as claimed in claim 1 and further comprising a stabilizing pad connected to said shroud for stabilizing said shroud against the oral structures to be masked.

4. A dental impression shroud as claimed in claim 3 wherein said oral structures comprise the teeth and soft tissue and said stabilizing pad is shaped to engage teeth on an opposite side of the jaw from the selected oral structures.

5. A dental impression shroud as claimed in claim 4 and further comprising a spring connecting said shroud and said pad, said spring being biased to urge both the shroud and pad against the respective oral structures.

6. A dental impression shroud as claimed in claim 1 wherein said shroud is a lingual shroud shaped to fit against the lingual side of the teeth and soft tissue.

7. A dental impression shroud as claimed in claim 1 wherein said shroud is a buccal shroud shaped to fit against the buccal side of the teeth and soft tissue.

8. A dental impression shroud as claimed in claim 1 wherein said shroud further comprises a lingual shroud member and a buccal shroud member connected by an at least one elastic member, whereby in use, said at least one elastic member extends through a dental embrasure to urge said shroud members against their respective oral structures.

9. A dental impression shroud as claimed in claim 1 wherein said shroud further comprises a lingual shroud member and a buccal shroud member connected by at least one ligature, whereby in use, said at least one ligature extends through a dental embrasure to hold said shroud members against their respective oral structures.

10. A dental impression shroud as claimed in claim 1 and further comprising a bonding agent for temporarily bonding said shroud to said oral structures.

* * * * *